United States Patent [19]
Kashimura et al.

[11] Patent Number: 5,968,906
[45] Date of Patent: Oct. 19, 1999

[54] SUCRALFATE PREPARATIONS

[75] Inventors: Koji Kashimura; Koichi Ozawa, both of Tokyo, Japan

[73] Assignee: Chugai Seiyaku Kabushiki Kaisha, Tokyo, Japan

[21] Appl. No.: 08/875,748

[22] PCT Filed: Feb. 2, 1996

[86] PCT No.: PCT/JP96/00217

§ 371 Date: Aug. 4, 1997

§ 102(e) Date: Aug. 4, 1997

[87] PCT Pub. No.: WO96/23507

PCT Pub. Date: Aug. 8, 1996

[30] Foreign Application Priority Data

Feb. 2, 1995 [JP] Japan ...................................... 7-51669

[51] Int. Cl.$^6$ ........................... A61K 31/70; A01N 43/04
[52] U.S. Cl. ............................. 514/23; 514/27; 514/574; 514/926; 514/928
[58] Field of Search .................................. 514/27, 23, 574

[56] References Cited

U.S. PATENT DOCUMENTS 5,288,497  2/1994  Stanley ..................................... 424/440

FOREIGN PATENT DOCUMENTS

| | | |
|---|---|---|
| 2646604 | 11/1990 | France . |
| 59-78116 | 5/1984 | Japan . |
| 61-503031 | 12/1986 | Japan . |
| 89/05645 | 6/1989 | WIPO . |
| 91/03241 | 3/1991 | WIPO . |
| 9104034 | 4/1991 | WIPO . |

*Primary Examiner*—Rebecca Cook
*Attorney, Agent, or Firm*—Browdy and Neimark

[57] ABSTRACT

Sucralfate containing preparations which contain both an organic acid having at least two carboxyl groups or at least one carboxyl group in the molecule and sucralfate are described. The sucralfate containing preparations have enhanced sucralfate adhesion to the mucosal ulcer site even under a nonacidic condition and can be extensively applied not only to ulcers in the upper digestive tract such as esophagitis and duodenal ulcer but also to ulcers in the lower digestive tract such as proctitis and ulcerative colitis, as well as to dermal ulcers such as bedsores, stomatitis and the like.

17 Claims, No Drawings

SUCRALFATE PREPARATIONS

This is a 371 of PCT/JP96/00217 filed Feb. 2, 1996.

TECHNICAL FIELD

This invention relates to sucralfate containing preparations that can be applied to mucosal damage and the like in a nonacidic condition and, more particularly, it relates to sucralfate preparations containing both an organic carboxylic acid having at least two carboxyl groups or at least one hydroxyl group in the molecule and sucralfate.

BACKGROUND ART

Sucralfate is a medicine that is described in the Japanese Pharmacopoeia and commonly used as a therapeutic for gastric and duodenal ulcers. The mechanism of its action is known to be attributable to antipepsin and antacid effects and the like. Two principal effects of sucralfate are believed to be forming a highly adhesive gel under an acidic condition to cover an ulcerated surface and in binding with plasma proteins under an acidic condition to cover the ulcerated surface (i.e., a mucosa protecting action). However, for selective binding to the mucosal ulcer site, the formation of a gel under the acidic condition caused by gastric acid is essential and in areas where acids are absent such as the small intestine, colon and the skin, no chemical binding and adhesion to the ulcer site occurs, except by physical adsorption.

There have been very few cases of the application of sucralfate which has been provided with enhanced adhesion to mucous membranes as in the small intestine and colon and the only exception is found in Japanese Patent Public Disclosure No. 190127/1987, which describes the application of added, collagen to the wound site. In known cases of sucralfate application to ulcerative colitis, sucralfate suspensions prepared with methylcellulose, propylcellulose and the like being added as thickeners are administered by the enteral route (see Scand. J. Gastroenterol., vol. 24, pp. 1014, 1989, Endoscopy, vol. 18, pp. 115, 1986, etc.) but these preparations have encountered several problems, one of which is that adhesion to the ulcer site is not expected.

As for the addition of organic acids to sucralfate, Japanese Patent Publication No. 35130/1993 describes the case of adding a phosphate or citrate to a sucralfate suspension. In this case, the organic acid salts are utilized to enhance the dispersibility of the suspension. However, enhanced adhesion to the ulcer site is not expected. Japanese Patent Domestic Announcement No. 500052/1993 discloses the technique of preparing effervescent tablets by adding an organic acid and a carbonate to sucralfate. However, the purpose of this proposal is the application of effervescent sucralfate tablets to the stomach and the use of carbonates is not intended to enhance the adhesion to the ulcer site.

DESCRIPTION OF INVENTION

In view of the above-described problems of the prior art, the present inventors conducted intensive studies on sucralfate preparations which would provide for effective adhesion of sucralfate to the mucosal ulcer site under a nonacidic condition; as a result, they found that sucralfate preparations containing both an organic carboxylic acid having at least two carboxyl groups or at least one hydroxyl group in the molecule and sucralfate permitted enhanced adhesion of sucralfate to the mucosal ulcer site under a nonacidic condition and this finding has led to the accomplishement of the present invention.

BRIEF DESCRIPTION OF THE INVENTION

FIG. 1 is a graph showing the BSA binding ratios of various added organic carboxylic acids and their acid to sucralfate equivalent ratios.

The organic carboxylic acid to be used in the invention is one having at least two carboxyl groups or at least one hydroxyl group in the molecule. Among such organic carboxylic acids, those which have at least 5% solubility, preferably at least 10% solubility, in water can be used with advantage.

As for the acid dissocation constant (pKl) of the organic carboxylic acid to be used in the invention, values of no more than 4 are preferred. Organic carboxylic acids having pKl values of more than 4 will not react readily with sucralfate and they are not expected to achieve enhanced adhesion which is the principal object of the invention.

Organic carboxylic acids that satisfy these conditions include citric acid, malic acid, maleic acid, tartaric acid, lactic acid, gluconic acid and glucuronic acid, with citric acid and malic acid being preferably used. Malic acid is more preferred.

The compositional ratio of the organic carboxylic acid to sucralfate in the sucralfate preparation of the invention ranges typically from 1:1 to 1:20, preferably from 1:3 to 1:10, on a weight basis with the lower limit being between 1:1 and 1:3 and the upper limit between 1:15 and 1:20. If the compositional ratio of the organic carboxylic acid is less than the above-mentioned range, sucralfate will not be adherent; in the opposite case, the organic carboxylic acid may dissolve the sucralfate or the irritating effect of the excess organic carboxylic acid may come into play and either situation is not suitable for practical preparations.

The above-mentioned organic carboxylic acids may be as a powder or a solution in the preparation. Sucralfate and the organic carboxylic acid may be present as separate entities in the preparation or, alternatively, they may be preliminarily reacted with each other before use.

The sucralfate to be used in the invention may be of any type such as one commercially available under the trade name of "Ulcerlmin" (registered trademark of Chugai Pharmaceutical Co., Ltd.) or one obtained by various synthesis procedures. When it is to be synthesize, sucralfate may be produced by the methods described in, for example, Japanese Patent Publication Nos. 11673/1969, 16037/1969 and 76927/1993, International Publication WO 9204030, etc. The wet powder which is obtained in each of the synthesis procedures or the sucralfate obtained by drying said powder may also be employed.

The sucralfate preparation of the invention may be used in various dosage forms including tablets, granules, subtilized granules, capsules, powders, troches, suppositories, pills, chewable tablets, solutions, emulsions, suspensions, lotions, ointments, cataplasms and elixirs. Pharmaceutical formulation of these dosage forms may be performed with various ancillaries added, such as pharmacologically acceptable suitable liquid or solid vehicles, excipients, dispersants, fillers, bulking agents, solvents, emulsifiers, additives, lubricants, antiseptics, flavoring agents, wetting agents, flavor correctives, dyes and buffers.

Solid preparations such as tablets, granules, subtilized granules, capsules, powders, troches, pills and chewable tablets can be formulated by the conventional procedures in the presence of various additives including vehicles such as sodium bicarbonate, calcium carbonate, starches, sucrose, mannitol and carboxymethylcellulose. These preparations are preferred for peroral administration and applicable to ulcers in the upper digestive tract such as esophagitis and duodenal ulcer.

If desired, enteric coatings of cellulose acetate phthalate, hydroxypropyl methylcellulose phtalate, polyvinyl alcohol phthalate, styrene-maleic anhydride copolymer and methacrylic acid-methyl methacrylate copolymer may be applied to formulate enteric preparations which will disintegrate in the small intestine, colon and the like.

To formulate solid preparations, sucralfate and an organic carboxylic acid may be individually granulated or otherwise processed in the pressence of suitable added ancillaries such as excipients and mixed into a powder, which is administered either by itself or after being shaped into capsules, tablets and the like. Alternatively, sucralfate dispersed in water may be reacted with an organic carboxylic acid and the reaction product is dried to form a powder, which may similarly be shaped into capsules, tablets and the like.

Solutions may be formulated using solvents exemplified by purified water, physiological saline, alcohols such as ethanol, propylene glycol, glycerin and polyethylene glycol, and triacetin. To formulate solutions, sucralfate and an organic carboxylic acid are placed in separate containers in the form of a suspension, solution or powder and, just before use, water is optionally added and the two ingredients are mixed together to form the solution. Alternatively, the two ingredients may be preliminarily reacted with each other to form the solution.

To treat proctitis, ulcerative colitis and other diseases in the lower digestive tract, suspensions, solutions and the like may preferably be put into enemic containers to formulate enemas or suppositories may be formulated for administration by the enteral route. Alternatively, enteric granules, tablets, capsules, etc. may be formulated for peroral administration. In other cases, sucralfate and an organic carboxylic acid may be processed into a gel in the presence of added water and a suitable base is added as required to formulate preparations for external application such as ointments and creams, which may be applied to dermal ulcers such as bedsores, as well as ulcers of the oral mucosa such as stomatitis. For the treatment of dermal ulcers such as bedsores, powders, suspensions and the like may also be formulated; for the treatment of ulcers of the oral mucosa such as stomatitis, troches, suspensions, powders, granules, tablets and the like may also be formulated.

Hydrophilic polymers may be added to the scralfate preparation of the invention to thereby impart viscosity such that the retention in the ulcer site and the mucosal affinity are enhanced. Exemplary hydrophilic polymers that may be employed for this purpose include alginic acid, sodium alginate, hydroxypropyl starch, a propylene glycol ester of alginic acid, methylcellulose, hydroxypropyl cellulose, hydroxypropyl methylcellulose, carboxymethyl cellulose, carboxymethycellulose sodium, carboxymethyl starch and carboxy vinyl polymers.

If the sucralfate preparation of the invention is to be used as a suspension, starches and/or starch derivatives are preferably used as dispersants and exemplary starches and/or starch derivatives include wheat starch, rice starch, corn starch, potato starch, glutinous corn starch, glutinous rice starch, starch acetic acid esters, starch succinic acid esters, starch nitrate esters, starch phosphate esters, starch xanthogenic acid esters, starch allyl ether, starch methyl ether, starch carboxymethyl ether, starch hydroxyethyl ether and starch hydroxypropyl ether (hydroxypropyl starch), with hydroxypropyl starch being preferably used.

The scralfate preparation of the invention may be administered either orally or parenteraly such as by the enteral, buccal and topical routes. The dosage can be selected as appropriate for the dosage form to be administered, the sex of the patient, physical makeup, constitution, age, etc.; typically, the drug may be applied 1–4 times a day, with the single dose being 5–200 mg/kg, preferably 10–100 mg/kg.

The invention will now be described in greater detail with reference to the following examples, which are by no means intended to limit the invention.

EXAMPLE 1

Sucralfate and an organic carboxylic acid (citric acid, malic acid, maleic acid, lactic acid, gluconic acid or glucuronic acid) were added to 15 ml of a physiological saline solution of 0.5% bovine serum albumin (BSA) in amounts that were weighed to give a sucralfate to BSA ratio of 0.05, 0.1 or 0.15. Following incubation at 37° C. for 30 min, the mixture was increased in volume up to 100 ml and passed through a 0.22-$\mu$m membrane filter to remove the BSA bound complexes, thereby preparing a sample solution. The percentage of BSA binding was determined by measuring the quantity of BSA in the solution with a protein assay reagent and the amount of sucralfate that would give 50% binding was determined. This was compared with the value of 50% sucralfate level as measured in a CLB buffer solution containing only sucralfate and the resulting ratio was designated as a BSA binding ratio. This value represents the ease in binding to proteins and provides an index of adhesion to the ulcer site. The BSA binding ratios of systems having various organic carboxylic acids and control HCl added are shown in FIG. 1.

With citric acid, malic acid, maleic acid, latic acid, gluconic acid and glucuronic acid, higher values were exhibited than with HCl and particularly high values were exhibited with citric acid and malic acid.

EXAMPLE 2

Japanese albino rabbits were injected with 0.2 ml of 3% acetic acid solution via a catheter through the anal portal to thereby create an acetic acid ulcer; one day later, sucralfate was mixed with citric acid and water to prepare a sample in a gel form, which was administered by the enteral route via a catheter in an amount equivalent to 100 mg/kg of sucralfate. At 3 hr after the administration, the rabbits were bled to death and the large intestine was removed and both the ulcer and healthy sites were sampled, each in a width of 1 cm; the adherent aluminum was extracted and assayed by atomic absorption spectroscopy. The results are shown in Table 1.

TABLE 1

| Sucralfate: citric acid (weight ratio) | Adhesion to ulcer site (ppm) (Al $\mu$g/cm$^2$) | Adhesion to healthy site (ppm) (Al $\mu$g/cm$^2$) |
| --- | --- | --- |
| 8:0 | 44.6 | 14.3 |
|  | (89.2) | (28.6) |
| 8:1 | 65.9 | 19.0 |
|  | (131.8) | (38.0) |
| 6:1 | 76.3 | 16.6 |
|  | (152.6) | (33.2) |
| 4:1 | 199.4 | 22.3 |
|  | (398.8) | (44.6) |
| 3:1 | 272.1 | 16.9 |
|  | (544.2) | (33.8) |

Table 1 shows, the incorporation of citric acid was effective in causing the sucralfate to adhere to the ulcer site selectively, with the adhesion being up to 5 times as large as in the case of sucralfate to which citric acid was not added.

EXAMPLE 3

As in Example 2, an acetic acid ulcer was created in the large intestines of Japanese albino rabbits. A sucralfate preparation was formulated by adding malic acid to a 10% sucralfate suspension containing 2.5% hydroxypropyl starch gel and it was administered by the enteral route with a catheter in an amount equivalent to 100 mg/kg of sucralfate. At 3 h after the administration, the rabbits were bled to death and the large intestine was removed and both the ulcer and anal sites were sampled; the adherent aluminum was extracted and quantitated. The results are shown in Table 2.

TABLE 2

| Sucralfate: malic acid (weight ratio) | Adhesion to ulcer site ($\mu g/cm^2$) | Adhesion to healthy site ($\mu g/cm^2$) |
| --- | --- | --- |
| 8:0 | 2.26 | 1.95 |
| 8:1 | 2.36 | 0.52 |
| 6:1 | 38.1 | 12.3 |
| 4:1 | 51.7 | 13.8 |

As Table 2 shows, the sucralfate in the sucralfate suspension which would readily disperse in the intestines adhered to the ulcer site selectively; it was therefore found that the sucralfate adhesion had been increased by the addition of malic acid.

EXAMPLE 4

The ingredients set forth in the following recipe were weighed, mixed and compressed to prepare tablets each weighing 293 mg.

| | |
| --- | --- |
| Sucralfate, dried powder | 200 mg |
| Citric acid | 50 mg |
| Carboxymethylcellulose calcium | 12.5 mg |
| Crystalline cellulose | 30 mg |
| Magnesium stearate | 0.5 mg |

EXAMPLE 5

The ingredients set forth in the following recipe were weighed, mixed and filled into capsules. By subsequent coating with a coating solution (see below) to give a solids content of 10%, enteric capsules were prepared.
(Capsule recipe)

| | |
| --- | --- |
| Sucralfate, dried powder | 80 parts |
| Citrid acid | 20 parts |
| Macrogol 6000 | 10 parts |

(Coating recipe)

| | |
| --- | --- |
| Hydroxypropyl methylcellulose phthalate | 10 parts |
| Macrogol 6000 | 1 part |
| Stearic acid | 2 parts |
| Methylene chloride | 50 parts |
| Ethanol | 50 parts |

EXAMPLE 6

As in Example 2, an acetic acid ulcer was created in the large intestines of Japanese albino rabbits. A sucralfate preparation (A) was formulated by adding 1 ml of 19.2% malic acid to 10 ml of 10% sucralfate suspension containing 2.5% hydroxypropyl starch gel; another sucralfate preparation (B) was formulated by the same procedure except that no aqueous malic acid solution was added. Each of the sucralfate preparations was administered by the enteral route with a catheter in an amount equivalent to 100 mg/kg of sucralfate. At 1 h, 3 h and 6 h after the administration, the rabbits were bled to death and the large intestine was removed and the aluminum adhering to the ulcer site was extracted and quantitated. The respective amounts of adhesion were converted to the sucralfate level. The results are shown in Table 3.

TABLE 3

| | Group of preparation (A) ($\mu mol/cm^2$) | Group of preparation (B) ($\mu mol/cm^2$) |
| --- | --- | --- |
| 1 h | 0.4722 ± 0.2483 | 0.0608 ± 0.0571 |
| 3 h | 0.1417 ± 0.0522 | 0.0140 ± 0.0305 |
| 6 h | 0.1417 ± 0.0990 | 0.0046 ± 0.0082 |

EXAMPLE 7

The ingredients set forth in the following recipe were weighed and mixed thoroughly to prepare powders.

| | |
| --- | --- |
| Sucralfate, dried powder | 800 mg |
| Malic acid | 160 mg |
| Mannitol | 35 mg |
| Precipitated silicic anhydride | 5 mg |

EXAMPLE 8

The ingredients set forth in the following recipe were weighed, mixed and compressed to prepare troches each weighing 1,600 mg.

| | |
| --- | --- |
| Sucralfate, dried powder | 1,000 mg |
| Malic acid | 300 mg |
| Polyethylene glycol 6000 | 200 mg |
| Sucrose | 80 mg |
| Sodium saccharin | 10 mg |
| Flavoring agent | 10 mg |

EXAMPLE 9

The ingredients set forth in the following recipe were weighed; hydroxypropyl starch was gelatized with 10 volumes of purified water and mixed with the respective ingredients to prepare suspensions.

| | |
| --- | --- |
| Sucralfate, dried powder | 1,000 mg |
| Lactic acid | 250 mg |
| Hydroxypropyl starch | 200 mg |
| Parahydroxybenzoic acid methyl ester | 3 mg |
| Parahydroxybenzoic acid propyl ester | 2 mg |
| Flavoring agent | 10 mg |
| Absolute ethanol | 50 mg |
| Purified water to make | 10 ml |

EXAMPLE 10

The ingredients set forth in the following recipes were weighed; using a 5% aqueous solution of hydroxypropyl cellulose as a binder, each of granulations 1 and 2 was kneaded and forced through a screen to prepare granules; the two batches of granules were mixed to prepare granules.

Granulation 1:

| Sucralfate, dried powder | 1,000 mg |
|---|---|
| Corn starch | 50 mg |
| Hydroxypropyl celulose | 10 mg |

Granulation 2:

| Tartaric acid | 300 mg |
|---|---|
| Lactose | 500 mg |
| Corn starch | 100 mg |
| Hydroxypropyl cellulose | 10 mg |

EXAMPLE 11

The ingredients set forth in the following recipe were weighed, mixed and compressed to prepare chewable tablets each weighing 2,000 mg.

| Sucralfate, dried powder | 1,000 mg |
|---|---|
| Glucuronic acid | 300 mg |
| Polyethylene glycol 6000 | 100 mg |
| Sucrose | 590 mg |
| Aspartame | 10 mg |

EXAMPLE 12

The ingredients set forth in the following recipe were weighed, dispersed in a fused base, agitated and shaped to prepare suppositories of 230 mg.

| Sucralfate, dried powder | 1,000 mg |
|---|---|
| Glucuronic acid | 300 mg |
| Polyethylene glycol 1540 | 1,400 mg |
| Polyethylene glycol 6000 | 600 mg |

EXAMPLE 13

The ingredients set forth in the following recipe were weighed and mixed well to prepare an ointment.

| Sucralfate, dried powder | 10 parts |
|---|---|
| Maleic acid | 4 parts |
| hydrophilic ointment JP | 86 parts |

INDUSTRIAL APPLICABILITY

The sucralfate preparation of the invention is capable of enhancing the adhesion of sucralfate to the mucosal ulcer site under a nonacidic condition and can be applied not only to ulcers in the upper digestive tract such as esophagitis and duodenal ulcer but also to ulcers in the lower digestive tract such as proctitis and ulcerative colitis, as well as to dermal ulcers such as bedsores, stomatitis and the like.

We claim:

1. A sucralfate preparation comprising group malic acid and sucralfate.

2. A preparation consisting essentially of an organic carboxylic acid having at least two malic acid sucralfate, optionally a hydrophilic polymer, and optionally a pharmaceutically acceptable carrier.

3. The preparation according to claim 1, wherein the ratio of the malic acid to the sucralfate is from 1:1 to 1:20.

4. The preparation according to claim 3, wherein the ratio of the malic acid to the sucralfate is from 1:3 to 1:10.

5. The preparation according to claim 1 which further has a hydrophilic polymer added thereto.

6. The preparation according to claim 5, wherein the hydrophilic polymer is a member selected from the group consisting of alginic acid, sodium alginate, hydroxypropyl starch, a propylene glycol ester of alginic acid, methylcellulose, hydroxypropyl cellulose, hydroxypropyl methylcellulose, carboxymethylcellulose, carboxymethylcellulose sodium, carboxymethyl starch and a carboxyvinyl polymer.

7. The preparation according to claim 1 which has a dosage form selected from the group consisting of a suspension, powder, non-chewable tablet, capsule, granule, suppository, ointment, chewable tablet and troche.

8. A method of treating proctitis which comprises administering to a patient in need thereof a therapeutically effective amount of the preparation of claim 1.

9. A method of treating ulcerative colitis which comprises administering to a patient in need thereof a therapeutically effective amount of the preparation of claim 1.

10. A method of treating esophagitis which comprises administering to a patient in need thereof a therapeutically effective amount of the preparation of claim 1.

11. A method of treating esophagitis which comprises administering to a patient in need thereof a therapeutically effective amount of the preparation of claim 1.

12. A method for the treatment of dermal ulcers which comprises applying to a dermal ulcer of a patient in need of said treatment a therapeutically effective amount of the preparation according to claim 1.

13. The method according to claim 12, wherein the patient's dermal ulcer is a bedsore.

14. A method for the treatment of stomatitis comprising administering to a patient in need thereof a therapeutically effective amount of the preparation according to claim 1.

15. The sucralfate preparation of claim 2 having said hydrophilic polymer.

16. The sucralfate preparation according to claim 15, wherein the hydrophilic polymer is a member selected from the group consisting of alginic acid, sodium alginate, hydroxypropyl starch, a propylene glycol ester of alginic acid, methylcellulose, hydroxypropyl cellulose, hydroxypropyl methylcellulose, carboxymethylcellulose, carboxymethylcellulose sodium, carboxymethyl starch and a carboxyvinyl polymer.

17. The sucralfate preparation according to claim 2 having a dosage form selected from the group consisting of a powder, a non-chewable tablet, a capsule, a granule, a suppository, an ointment, a chewable tablet and a troche.

* * * * *